United States Patent
Brands et al.

(10) Patent No.: US 11,103,562 B2
(45) Date of Patent: Aug. 31, 2021

(54) COMPOSITION COMPRISING ALKALINE PHOSPHATASE FOR USE IN THE TREATMENT OF ARTHRITIDES

(71) Applicant: AMRIF BV, Wageningen (NL)

(72) Inventors: Rudi Brands, Bunnik (NL); Willem Seinen, Bilthoven (NL); Carolina Frederika Maria Molthoff, Ouderkerk aan de Amstel (NL); Gerrit Jansen, Loenen aan de Vecht (NL); Ronald Sake Oosting, Soest (NL)

(73) Assignee: AMRIF BV, Wageningen (NL)

( * ) Notice: Subject to any disclaimer, the term of this patent is extended or adjusted under 35 U.S.C. 154(b) by 83 days.

(21) Appl. No.: 16/469,542

(22) PCT Filed: Dec. 12, 2017

(86) PCT No.: PCT/EP2017/082337
§ 371 (c)(1),
(2) Date: Jun. 13, 2019

(87) PCT Pub. No.: WO2018/127363
PCT Pub. Date: Jul. 12, 2018

(65) Prior Publication Data
US 2020/0121765 A1    Apr. 23, 2020

(30) Foreign Application Priority Data
Jan. 5, 2017  (EP) .................. 17150448

(51) Int. Cl.
*A61K 38/46* (2006.01)
*A61K 31/519* (2006.01)
*A61P 19/02* (2006.01)
*A61K 9/00* (2006.01)

(52) U.S. Cl.
CPC .......... *A61K 38/465* (2013.01); *A61K 9/0029* (2013.01); *A61K 9/0053* (2013.01); *A61K 31/519* (2013.01); *A61P 19/02* (2018.01); *C12Y 301/03001* (2013.01)

(58) Field of Classification Search
CPC ... A61P 19/02; A61P 19/00; C12Y 301/03001
See application file for complete search history.

(56) References Cited

U.S. PATENT DOCUMENTS

| 2009/0232731 A1 | 9/2009 | Funk et al. |
| 2011/0206654 A1 | 8/2011 | Hodin et al. |
| 2016/0199415 A1 | 7/2016 | Ghosh et al. |

FOREIGN PATENT DOCUMENTS

| WO | WO2008104200 A1 | 9/2008 |
| WO | WO2015112017 A1 | 7/2015 |

OTHER PUBLICATIONS https://www.rheumatology.org/I-Am-A/Patient-Caregiver/Treatments/Sulfasalazine-Azulfidine retrieved using wayback machine Mar. 1, 2016 (Year: 2016).*
ESGCT and FSGT Collaborative Congress Helsinki, Finland Sep. 17-20, 2015 Abstracts, Human Gene Therapy, Sep. 17, 2015 (Sep. 17, 2015), XP055215257, ISSN: 1043-0342, DOI: 10.1089/hum.2015.29008.abstracts.

* cited by examiner

*Primary Examiner* — Michelle F. Paguio Frising
(74) *Attorney, Agent, or Firm* — Bret E. Field; Bozicevic, Field & Francis LLP

(57) ABSTRACT

Present invention relates to a composition for use in the treatment of arthritides. Alkaline phosphatase (AP), an ectophosphatase with an anti-inflammatory and barrier protecting mechanism of action shows potent anti-rheumatoid arthritis (anti-RA) efficacy in a rat model for arthritis. In this model RA was induced by subcutaneous immunization with a mixture of methylated bovine serum albumin (mBSA), CFA (complete Freund's adjuvant antigen) and CBP (custom Bordetella pertussis antigen) and intra-articular injections of mBSA. Results were comparable with those obtained for MTX, the drug reference compound for the treatment of RA. Both knee swelling over time and the number of invading macrophages were found to be reduced with AP treatment, either applied in prophylactic treatment or therapeutic treatment, and comparable to the MTX effects. AP was found effective both as prophylactic, and as therapeutic intervention. Altogether, ectophosphatase intervention by AP fulfills a novel and unmet niche in RA treatment by combining different, yet synergistic mode of actions with MTX.

17 Claims, 12 Drawing Sheets

A control knee

B Rheumatoid Arthritic knee

A

B

ED1 macrophages

ED2 macrophages

PBS- treated

AP-treated

Figure 1:
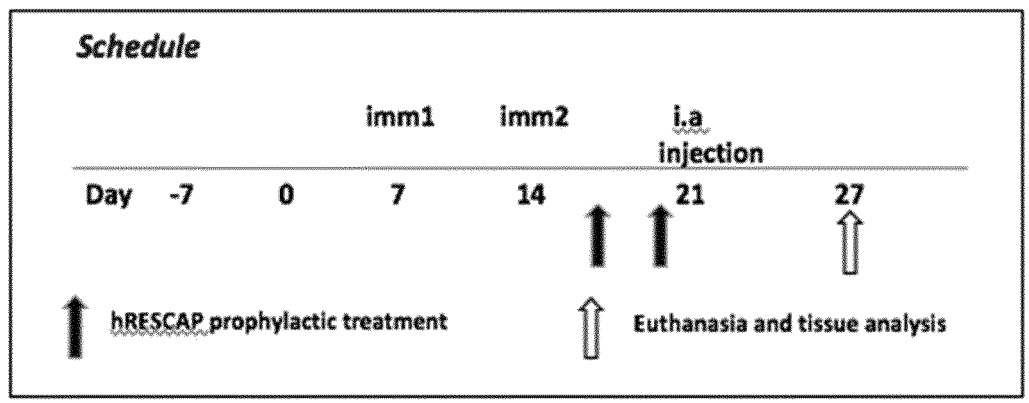
Figure 1:
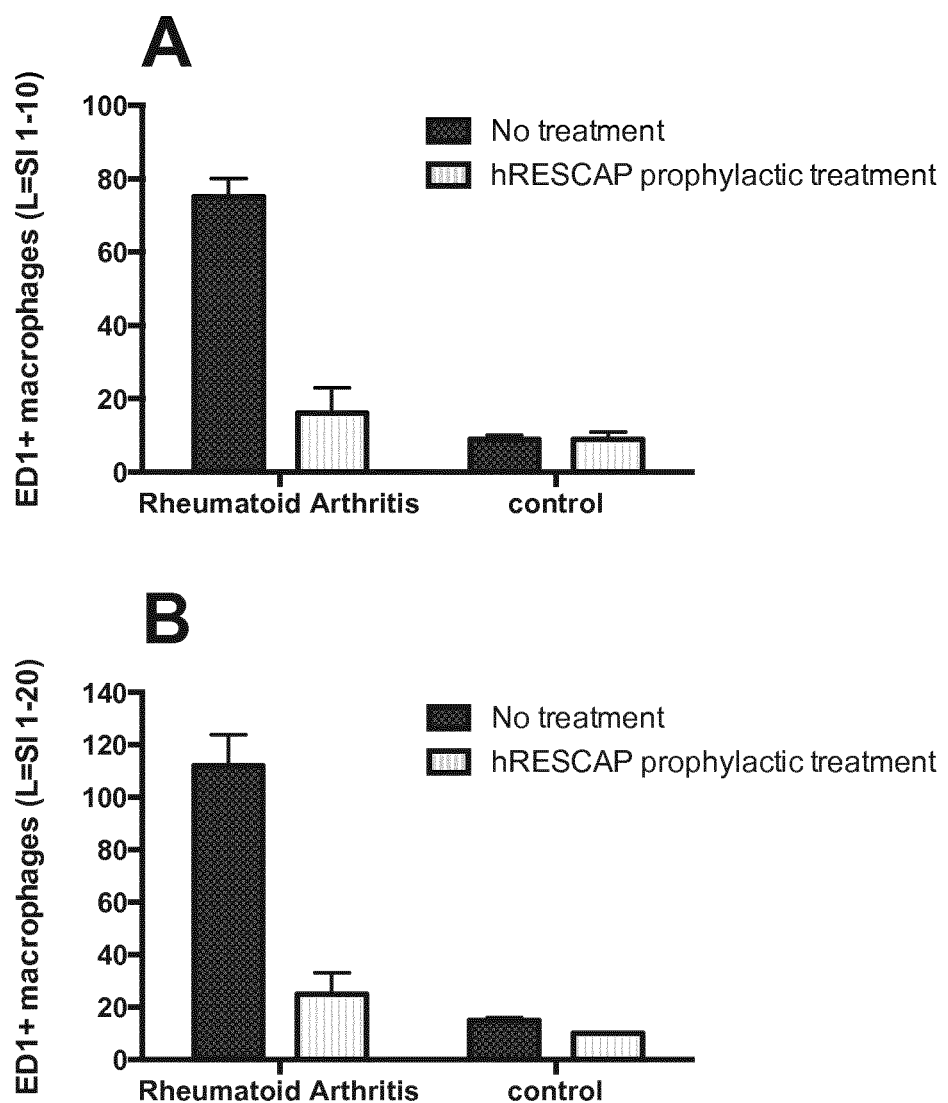

COMPOSITION COMPRISING ALKALINE PHOSPHATASE FOR USE IN THE TREATMENT OF ARTHRITIDES

Present invention relates to a composition for use in the treatment of arthritides (also designated herein as arthritis).

Arthritides are a group of over 100 varieties of inflammatory or degenerative diseases that damage joints, involving pain or stiffness of the musculoskeletal system. Arthritis is an inflammation of a joint or joints. The most common types are osteoarthritis and Rheumatoid Arthritis (RA), Gout, Ankylosing spondylitis, but also can be secondary to other diseases like Psoriatic arthritis, Systemic Lupus Erythematosus. Examples of arthritis (not of acute forms) include osteoarthritis, rheumatoid arthritis, and gouty arthritis. Acute forms are commonly caused by bacterial invasion.

Although its pathogenesis is unknown, RA is characterized by chronic inflammation in multiple joints, which develops into erosion of marginal bone and cartilage, juxta-articular bone loss, and a general reduction in bone mass. It is widely accepted that inflammatory cells, especially lymphocytes and macrophages, are crucial players in the pathogenesis of RA, and that cytokines, such as tumour necrosis factor α (TNFα), interleukin 1 (IL-1), IL-6 and IL-8, are also involved. In addition, recent findings have shown that osteoclasts play a key role in joint destruction and osteoporosis in RA, without being balanced by osteoblastic activity (hence osteoclastic activity/osteoblastic activity >1). Although RA manifests itself as a joint disease, the root cause of RA may originate systemic. RA patients show increased levels of plasma levels IL-1, IL-6 and TNFα (during exacerbations or chronic disease manifestation) indicative for a pro-inflammatory state physiological condition.

Rheumatoid arthritis (RA) is a major systemic autoimmune disease, associated with high morbidity and mortality—50% of the RA patients are too disabled to work 10 years after disease onset—and shortens life span by 3 to 18 years. RA is associated with significant higher medical costs and lost working time.

Albeit that the causal root factor or mechanism leading to RA is not yet known, a role of systemic triggers of inflammation in aggravation or induction of RA has been proposed. For instance, there seems to be a correlation between the activity and extent of the intestinal disease and the severity of arthritis. Small bowel bacterial overgrowth induces RA and recombinant bactericidal/permeability-increasing protein, an agent that neutralizes endotoxin, and metronidazole, which is active against anaerobic bacteria, prevented arthritis induction. Next to gram-negative bacterial toxins (e.g. lipopolysaccharides), also gram-positive bacterial toxins (e.g. lipoteichoic acid) may induce arthritis. Next to bacterial toxins also bacterial-derived excess levels of ATP/ADP in gut drives a pro-inflammatory state. Also, collagen induced RA animal models have been described where, RA-induction failed in case the animals were raised under septic conditions. This indicates that bacterial components derived from commensal and pathogenic strains may influence local and systemic homeostasis and immune responses.

As there is no cure for rheumatoid arthritis, the goal of pharmacological management is to relieve symptoms, prevent joint damage and put the disease into remission. The "golden standard" disease-modifying anti-rheumatic drugs (DMARDs) used in the treatment of RA is Methotrexate (MTX). MTX has shown to clearly control the inflammatory response as first line agent. Its long-term efficacy is well documented, but rarely leads to a true/complete remission. A monotherapy with MTX is not often associated with sustained disease remissions. A major drawback of MTX is the cytotoxicity and nephrotoxicity and the negative effects to patients that are treated for a long time period. Only 50% of patients stay on MTX after 5 years due to its toxicity. Another disadvantage is that resistance to MTX is known to be induced and therefore MTX is often used in combination with other drugs.

Other disease modifying agents used in the treatment of RA are anti-tumour necrosis factor (TNF) drugs (e.g. Etanercept or Infliximab), so called TNFα blockers. For these types of drugs it has been shown to reduce disease activity, to have rapid improvement in joint pain and swelling, and reduce joint damage in patients suffering from RA shown. TNFα is an important cytokine that is involved in a number of pro-inflammatory effects and plays a major role in inflammatory diseases such as rheumatoid arthritis and is a key element in its pathogenesis. Current anti-TNFα drugs are used to block TNFα and thereby reducing the inflammatory response and potentially prevent or alleviate joint damage. Anti-TNFα drugs are used either as stand alone therapy or in combination therapy, with e.g. MTX.

However, the currently marketed biological TNFα blockers demonstrate several side effects. One of the foremost effects is the break of immune tolerance towards the antibody drug due to the non-natural nature of these drugs. This leads to the formation of inactivating antibodies and makes the applied dosages less effective. As a consequence the patient does not respond any longer to the beneficial effects of the compound. Patients then are re-introduced to other pharmaceuticals, like corticosteroids, that have major adverse implications for patient-specific time periods. Also, the use of anti-TNF antibodies may lead to increased risk to serious infections, in particular tuberculosis.

Considering the above, there is a need in the art for new strategies for the treatment of arthritis. Furthermore there is a need in the art for a treatment that has less adverse effects on patients during treatment and is more effective than the current treatments available.

It is an object of the present invention, amongst other objects, to address the above need in the art. The object of present invention, amongst other objects, is met by the present invention as outlined in the appended claims.

Specifically, the above object, amongst other objects, is met, according to a first aspect, by the present invention by an ectophosphatase in combination with a disease-modifying anti-rheumatic drugs (DMARDS) for use in the treatment of a mammal suffering from arthritis. Arthritis include for example osteoarthritis, rheumatoid arthritis (RA), and gouty arthritis. An inaccurate systemic response of the innate immune system during pro-inflammatory insults results in further progression of disease. Consequently, attenuating these flare-up (exacerbation)-mediated systemic inflammatory responses (e.g. cytokine storms) may prove beneficial Alkaline phosphatase (AP) fulfils this function, and hence can be applied as a routine therapeutic compound.

According to another aspect of present invention, the present invention relates to the an ectophosphatase in combination with a disease-modifying anti-rheumatic drugs (DMARDS) for use, wherein the DMARDS is methotrexate (MTX). Combination therapy with alkaline phosphatase will enable effective therapeutic regimes at lower doses of MTX when combination therapy is applied. MTX, applied at doses for anti-RA therapy results in the efflux of /release of intracellular nucleotides like ATP and ADP from cells and subsequently are converted into adenosine. Adenosine has potent anti-inflammatory impact and de-activates activated white blood cells that are causal to RA pathology. By deduction alkaline phosphatase thus will be synergistic to MTX therapy by enabling conversion into anti-inflammatory adenosine. Also nucleotides released from cells under oxidative stress like those in affected areas implicated with RA will be converted thereby generating an anti-inflammatory micro-environment in e.g. joints.

AP is a potent mitigator to e.g. TNFα responses in inflammatory conditions and AP activity results in significant attenuation of cytokine storms, as has been demonstrated in preclinical and clinical studies, e.g. in patients undergoing major surgery. Specifically sharp reductions were observed for pro-inflammatory markers like TNFα, IL-6 and IL-8, whereas IL-10 plasma levels were not much affected. The latter suggests that the basic pro-inflammatory triggering event does not occur in e.g. macrophages and other white blood cells in the presence of sufficient AP levels and as a consequence no anti-inflammatory IL10 is produced. Furthermore, in contrast to the current anti RA-agents that target one of the major cytokine intermediates, AP is proposed to be a gate keeper in the innate immune defence system, and affects multiple cytokines.

Alkaline phosphatase, a physiological effective and active endogenous protein in healthy conditions, does not have putative adverse effects like increased risk for infections and development of issues to tolerance or resistance. Given the fact that even at high endogenous levels of AP is safe to both mother and developing child as observed during pregnancy and well tolerated for prolonged time intervals, we envision that AP therapy may be of benefit towards advanced rheumatic patients.

Oxidative stress (e.g. Ischemic injury-) mediated down stream effects may result in release of nucleotides like ATP, ADP and AMP from affected cells. These normally intracellular residing moieties, involved in intracellular energy supply, are potent pro-inflammatory factors (inflammation triggering moieties, ITM) once they are in the extracellular environment. These ITM' s are detoxified by the activity of ectophosphatases like AP, CD39 and CD73. As a result of acting on ATP and ADP adenosine is generated, which has an antagonistic (anti-inflammatory) effect. Thus AP is proposed as single anti-inflammatory, and in this case a stand-alone effective, anti-RA agent or even in combination therapy with other agents. The advantage of the latter approach will be that doses required of such other pharmachemical or biological anti-RA compounds will be lower, thereby reducing the likeliness for induction of resistance or impact on tolerance.

According to yet another preferred embodiment, the present invention relates to the ectophosphatase in combination with a disease-modifying anti-rheumatic drugs (DMARDS) for use, wherein arthritis is rheumatoid arthritis.

According to present invention, a mammal suffering from arthritis, can be any vertebrate, such as a monkey, horse, cattle, rodent, human being, preferably a human being.

According to another preferred embodiment, the present invention relates to the ectophosphatase in combination with a disease-modifying anti-rheumatic drugs (DMARDS) for use, wherein the ectophosphatase is selected from the group consisting of alkaline phosphatase, CD39, and CD73. The source of such ectophosphatase can be multiple; derived from native sources or recombinant technology by expression of ectophosphatases in one-cellular organisms, like yeast, or multicellular organisms like plants or animals.

According to another preferred embodiment, the present invention relates to the ectophosphatase in combination with a disease-modifying anti-rheumatic drugs (DMARDS) for use, wherein the ectophosphatase is a recombinant alkaline phosphatase.

According to yet another preferred embodiment, the present invention relates to the ectophosphatase in combination with a disease-modifying anti-rheumatic drugs (DMARDS) for use, wherein the ectophosphatase is a recombinant mammalian alkaline phosphatase, preferably a human alkaline phosphatase. Preferably the phosphatase used in the combination of present invention is compatible with the foreseen therapeutic intervention that it is to support, e.g. the treatment of a human being using the composition of present invention comprising a recombinant human alkaline phosphatase. However also other combinations may be used, for instance the treatment of a human being using the composition of present invention comprising a non-human native or non-human recombinant alternative alkaline phosphatase, like e.g. bovine intestinal derived alkaline phosphatases.

The ectophosphatase in combination with a disease-modifying anti-rheumatic drugs (DMARDS) for use of present invention can be applied by either topical (e.g. oral, inhalation therapy) or parenteral administration, in a suitable formulation applicable for such routes of administration. Only after parenteral administration AP can act directly to the target. Most treatments of chronic inflammatory diseases like rheumatoid arthritis still require frequent and long-term administration, which utilizes conventional routes such as oral administration, intramuscular and intravenous injections, resulting in accumulation of drug outside the inflamed area and sometimes unwanted systemic side effects. Targeting can be made more specific by for example using nano-formulated AP.

According to yet another preferred embodiment, the present invention relates to the ectophosphatase in combination with a disease-modifying anti-rheumatic drugs (DMARDS) for use, further combined with nanoparticles. By loading the nanoparticles with the ectophosphatase of present invention or in combination with DMARDS, shown to be effective as such against RA, an effective treatment modality can be developed. Using nanoparticles for the delivery of the composition of present invention, drugs are specifically released at the inflamed area in a controlled or sustained manner consequently reducing unwanted effects and improve patient compliance.

According to a preferred embodiment, the present invention relates to the ectophosphatase in combination with a disease-modifying anti-rheumatic drugs (DMARDS) for use, wherein the nanoparticles are comprised of a material selected from the group consisting of fullerene, liposome, gold, poly lactic-co-glycolic acid (PLGA) and poly L-lactic acid (PLA). The nanoparticles that can be used to encapsulate the composition of present invention is preferably comprised of gold, poly lactic-co-glycolic acid (PLGA) or poly L-lactic acid (PLA), more preferably PLGA or PLA, most preferably PLGA.

A suited AP is preferably a recombinant human AP that has a prolonged plasma residence time. In this way, recombinant human AP may be positioned as a routine use alternative compound to the current agents applied in the treatment of RA.

In addition, the use of recombinant human AP will circumvent putative immunological responses that may follow prolonged use of non-human like (glyco-)proteins, such as bovine AP that is applied in cardiac surgery for short-term use only. Typical for glycoproteins with warranted prolonged plasma residence time is a fully complex glycosylated oligosaccharide chain. Most of the potential sources for AP do not have sufficient complex sugar-chains attached and consequently demonstrate plasma residence times that are a fraction of the preferred therapeutics. Albeit alternative non-human AP, like bovine AP has significant TNFα blocker activity even with these short residence times, it is assumed not to be very efficacious when used chronically. However, it may be used as "vacation drug (off-period drug use)" in short-term applications regimes in RA patients during their withdrawal period from therapy with currently applied TNFα blockers. Therefore these AP's are proposed here to act as "vacation drug". For temporary use application, as "vacation drug", several sources of AP can be used. Sources that are identified and from which biological relevant AP activity was established include native and recombinant APs expressed in e.g. yeast-, plant-, moss- and mammalian-expression models.

According to a preferred embodiment, the present invention relates to the ectophosphatase in combination with a disease-modifying anti-rheumatic drugs (DMARDS) for use, wherein the treatment comprises parenteral or oral administration of said composition. The therapeutic intervention can be applied by either topical (e.g. oral, inhalation therapy) or parenteral administration, in suitable formulation applicable for such routes of administration.

According to yet another preferred embodiment, the present invention relates to the ectophosphatase in combination with a disease-modifying anti-rheumatic drugs (DMARDS) for use, wherein the treatment comprises prophylaxis, or delay of onset, or attenuated progression of arthritis. Therefore the ectophosphatase in combination with a disease-modifying anti-rheumatic drugs (DMARDS) for use of present invention can be used as prophylaxis to prevent or reduce the inflammatory response during pro-inflammatory insults which results in the attenuation of further progression of disease. AP may also be used therapeutically for the treatment of a mammal suffering from arthritis.

According to another preferred embodiment, the present invention relates to the ectophosphatase in combination with a disease-modifying anti-rheumatic drugs (DMARDS) for use, wherein said treatment comprises attenuation of the inflammatory response of a mammal suffering from arthritis. The attenuation of the inflammatory response can also comprise the treatment of exacerbations of the patient suffering from arthritis.

According to yet another preferred embodiment, the present invention relates to the ectophosphatase in combination with a disease-modifying anti-rheumatic drugs (DMARDS) for use, wherein the ectophosphatase is a tissue specific ectophosphatase and the treatment is a chronic arthritis disease treatment.

According to a preferred embodiment, the present invention relates to the ectophosphatase in combination with a disease-modifying anti-rheumatic drugs (DMARDS) for use, wherein the tissue specific ectophosphatase is selected from the group consisting of intestinal AP (IAP), placental ALP (PALP) and liver AP (LAP), preferably placental ALP (PALP). Albeit that both tissue non-specific alkaline phosphatase (TNSALP) and tissue-specific AP like Intestinal-AP (IAP) cq Placental-ALP (PALP) share an activity towards nucleotides, as indicated by both in-vitro and in-vivo studies carried out in house, a significant difference in the molecular structure is found between TNSALP on the one side and IAP or PALP on the other side. The so-called crown domain that encompasses a RGD-binding site for bone-type AP in the TNSALP isozymes lacks in the tissue specific IAP and PLAP. We propose here that this crown domain is a homing moiety for the TNSALP and so, this would explain that e.g. intestinal ALP, albeit relatively increased in RA patients may compensate in part for nucleotide toxicity but not for bone formation. Preferably, alternatively the placental ALP may be used in RA patients. The safety of prolonged application of placental AP is warranted, since elevated plasma levels during pregnancy up to 30 fold normal levels are apparent. The increased plasma levels even correlate with reduced clinical RA symptoms in pregnant RA patients, possibly also because it reduces the need for endogenous tissue specific (bone, liver kidney AP) replenishment. It is known that in pregnant women placental ALP is significant upregulated during the second and last trimester of pregnancy and is cleared out of circulation with a half-life (T1/2) of 7 days. We would favour the administration of human Placental-ALP as chronic disease treatment in RA patients. Also it is described that the clinical phenotype of many auto-immune diseases are ameliorated during these trimesters, but reappear after pregnancy with the same kinetics as the clearance of placental AP. Human placental-ALP is an enzyme that is fully glycosylated exposing terminal sialic acid on its oligosaccharide side chains, and therefore is not cleared fast from circulation through the liver asialoglycoprotein receptor.

In principle, the intestinal AP-isoenzyme may also be used as it is very similar to placental type alkaline phosphatase, however we would propose to use rather placental over intestinal type due to its favourable plasma residence time of about 6-7 days, thereby being compatible with acceptable treatment regimes for chronic disease treatment. The intestinal isoenzyme, compared to the placental isoenzyme has short plasma residence time, making the intestinal enzyme ideal to be applied in specific acute therapeutic interventions, like major surgery where it combats ischemic injury mediated complications.

According to another preferred embodiment, the present invention relates to the ectophosphatase in combination with a disease-modifying anti-rheumatic drugs (DMARDS) for use, wherein the tissue specific ectophosphatase is selected from the group of intestinal AP (IAP), placental ALP (PALP) and liver AP (LAP), preferably IAP, more preferably PALP, or a combination thereof.

According to yet another preferred embodiment, the present invention relates to the composition, wherein the ectophosphatase is a tissue non specific ectophosphatase and said treatment is a non-chronic arthritis disease treatment.

According to a preferred embodiment, the present invention relates to the ectophosphatase in combination with a disease-modifying anti-rheumatic drugs (DMARDS) for use, wherein the ectophosphatase in combination with a disease-modifying anti-rheumatic drugs (DMARDS) for use, is administered at least once a month, preferably at least two times a month, more preferably at least three times a month, even more preferably at least four times a month, and most preferably at least five times a month. Furthermore the present invention relates to the composition, wherein the combination is administered at least once weekly, more preferably 2 times a month, preferably at least 3 weekly, more preferably at least once every month, and most preferably in periods extending one month periods. Furthermore the combination of present invention can be administered at least once every 2 months, preferably at least once every 3 months, more preferably at least once every 4 months, and most preferably at least once every 5 months. The combination of present invention may be administered at least once a week.

As mentioned above, the advantage of Placental AP (e.g. native placental AP or recombinant human alkaline phosphatase (hRESCAP)) over both intestinal and bone, liver or kidney isozyme supplementation is the extreme plasma residence time of 6-7 days. Given this T1/2 it allows for acceptable parenteral administration twice a month, whereas e.g. intestinal AP would have to be administered daily, which is not preferred in chronic treatment dosing schedules.

The present invention will be further detailed in the following example, the example relates to figures wherein:

FIG. 1: shows the effect of prophylactic AP treatment on ED1+synovial macrophages in arthritic rats (2× AP before intra articular antigen injection). Massive infiltration of activated macrophages (ED1+) is observed in the inflamed knees ("Rheumatoid Arthritis") of rats after immunization and intra articular boosting with methylated BSA (mBSA). The effect is observed in both lining and sublining, respectively 10 (FIG. 1A) and 20 cell layers deep (FIG. 1B). Note that control knees show only mild macrophage infiltration. Similar mild infiltration is observed after AP treatment ("hRESCAP prophylactic treatment") with even less reaction in the control knees of each of the rats.

Figure 2:
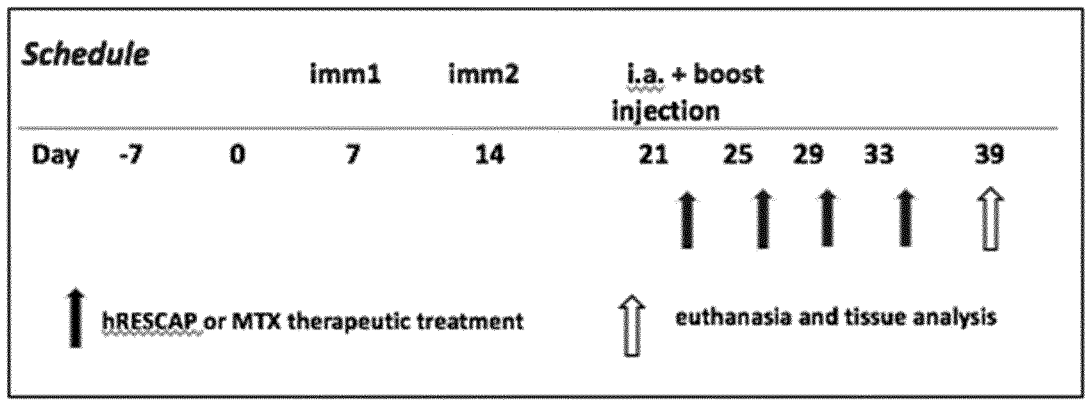
Figure 2:
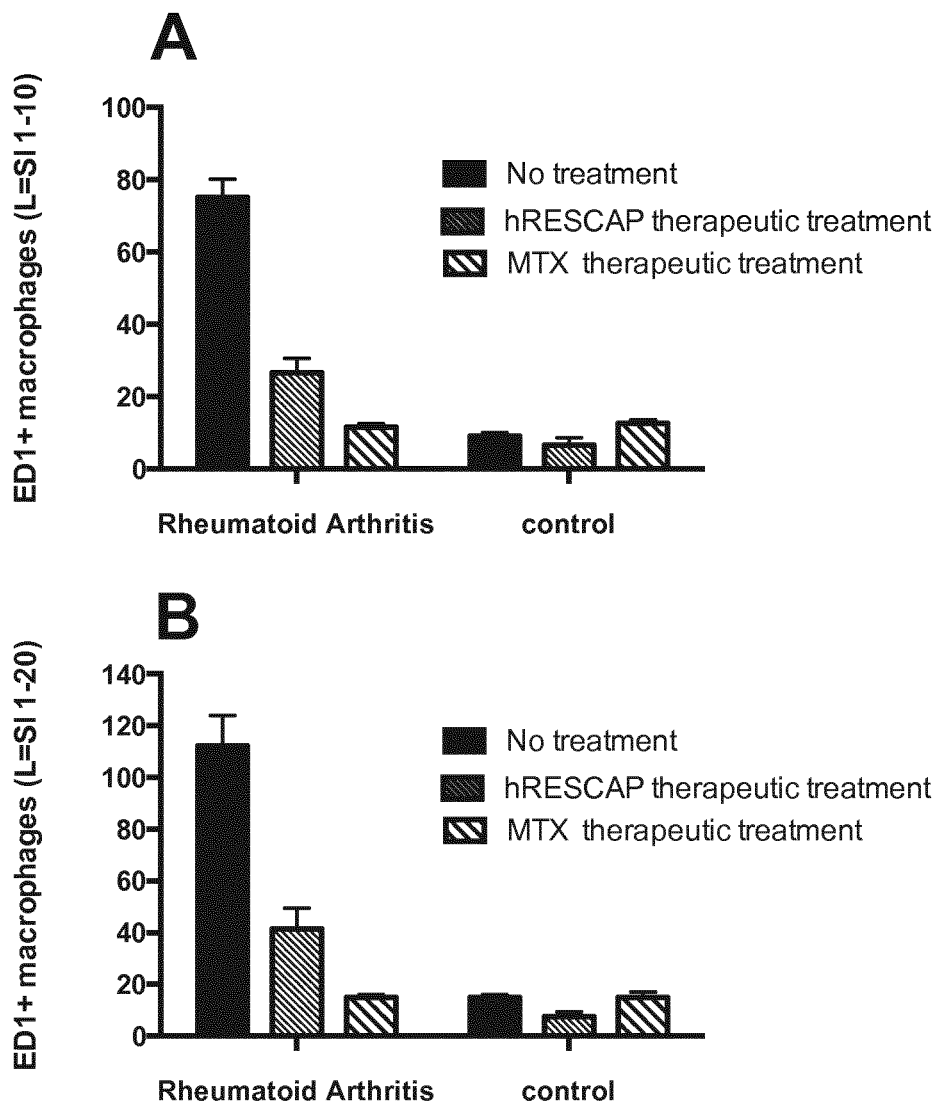

FIG. 2: shows the effects of AP therapeutic treatment on ED1+ synovial macrophages in arthritic rats (4× AP after first i.a. and in between boosts). The AP therapeutic treatment is compared with MTX treatment. Rats that show a positive effect after stimulation with mBSA in right knee by showing increased ED1+ macrophages, whereas AP-treated rats do not show this activity. The effect is observed in both lining and sublining, respectively 10 (FIG. 2A) and 20 cell layers deep (FIG. 2B). Note that AP treatment, given after the intra articular mBSA injection, reduces ED1+ infiltration. However, MTX treatment results in even more reduced macrophage ED1+ counts, but counts on the negative control knee appear to be higher than in AP treated rats.

Figure 3:
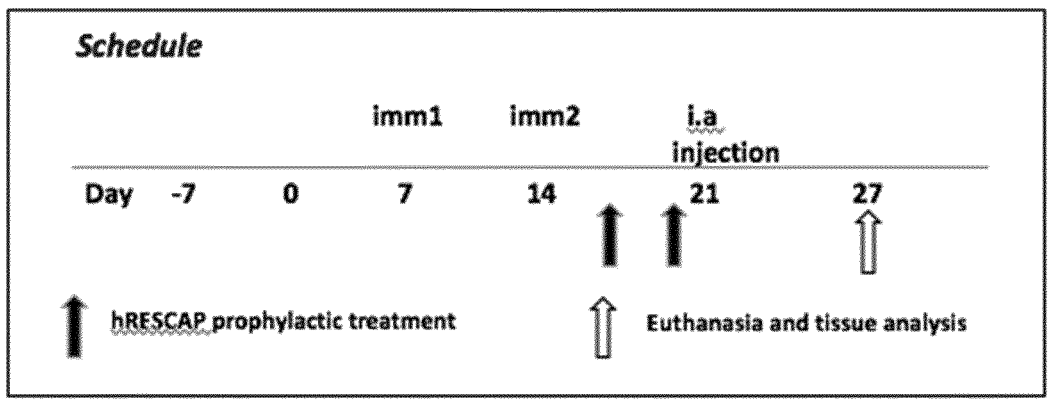
Figure 3:
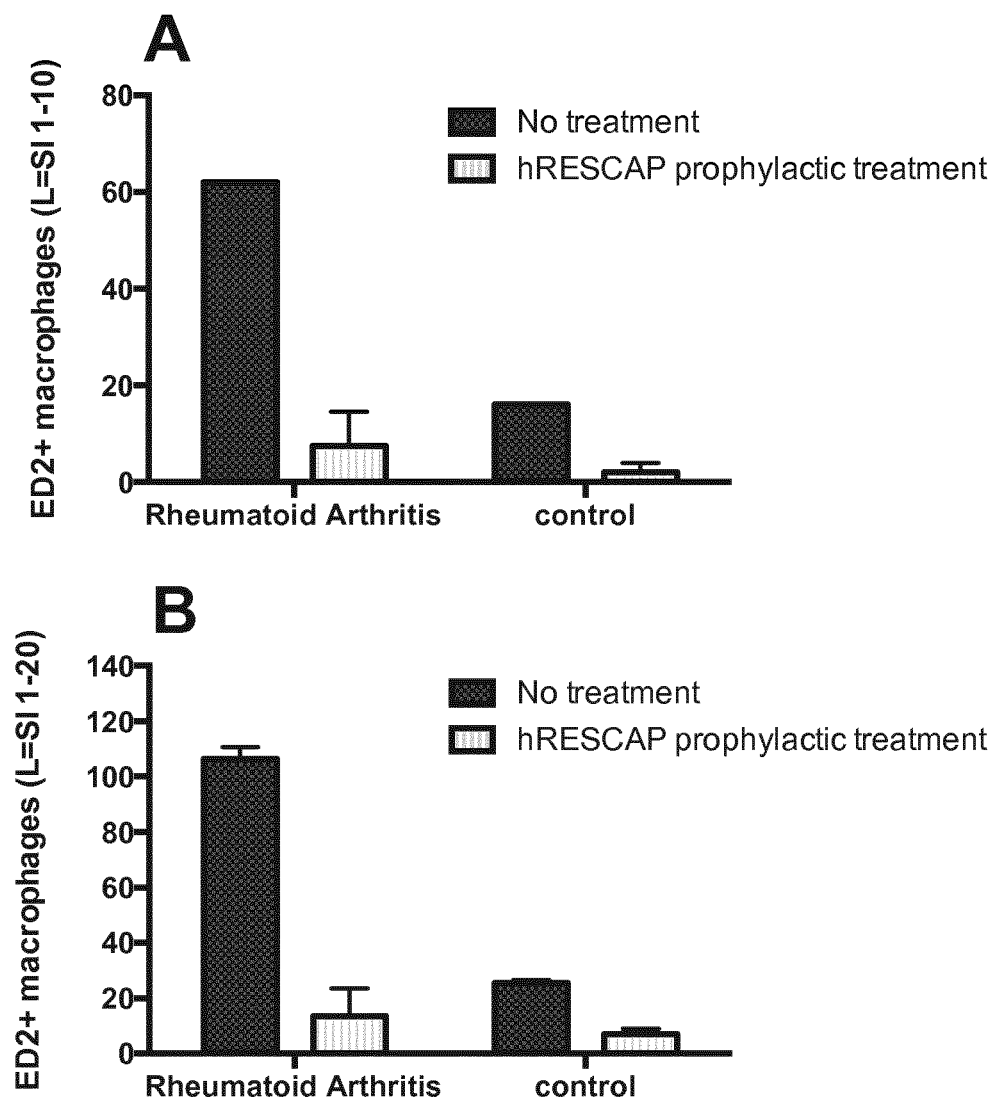

FIG. 3: shows the effect of AP treatment on ED2+ synovial macrophages in arthritic rats (2× AP before intra articular antigen injection). Rats that show a positive effect after stimulation with mBSA in right knee by showing increased ED1+ macrophages also show reaction of ED2+ activity, whereas AP treated rats do not show this activity. This is in line with the general idea of inducing an anti-inflammatory response only after a pro-inflammatory event has been given. The effect is observed in both lining and sublining, respectively 10 (FIG. 3A) and 20 cell layers deep (FIG. 3B). From this it is evident that the absence of a pro-inflammation event upon AP treatment is not followed by an anti-inflammatory response as seen by reduced ED2+ macrophage immune histochemistry read out.

Figure 4:
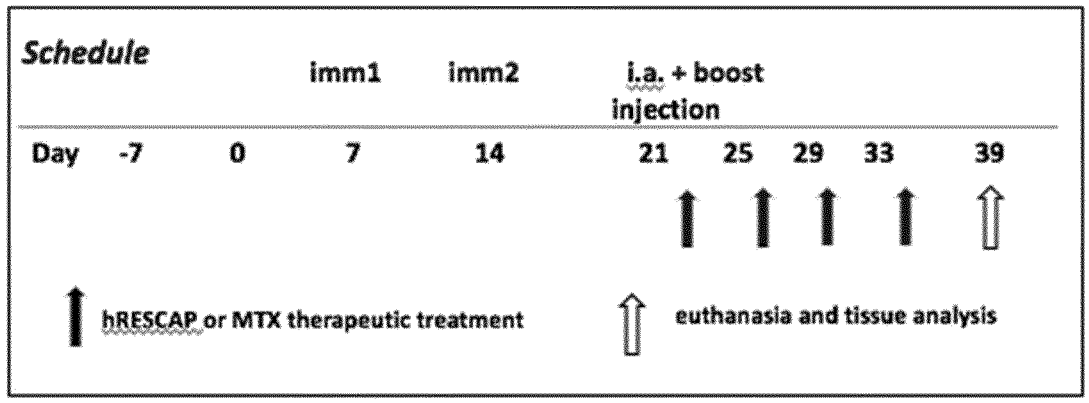
Figure 4:
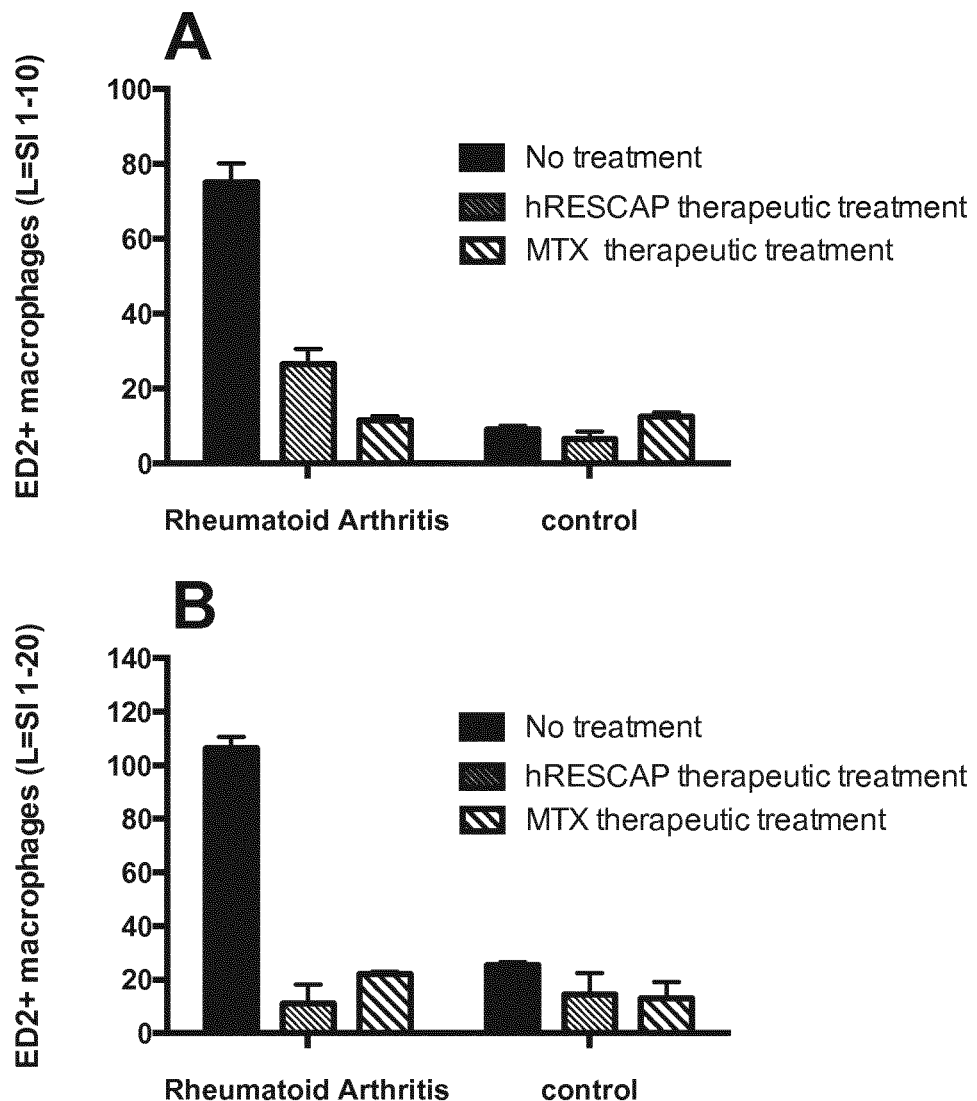

FIG. 4: shows the effects of AP treatment on ED2+ synovial macrophages in arthritic rats (4× AP after first i.a. and in between boosts). Rats that show positive control effect after stimulation with mBSA in right knee by showing increased ED1+ macrophages also show reaction of ED2+ activity, whereas AP treated rats do not show this activity. This is in line with the general idea of inducing an anti-inflammatory response only after a pro-inflammatory event has been given. From this it is evident that the absence of a pro-inflammation event upon AP therapeutic treatment also after intra articular injection with mBSA is not followed by an anti-inflammatory response as seen by reduced ED2+ macrophage immune histochemistry read out. Note that with AP treatment, also after intra articular mBSA injection, effects are much reduced and are very similar to the effects obtained with MTX treatment. The effect is observed in both lining and sublining, respectively 10 (FIG. 4A) and 20 cell layers deep (FIG. 4B).

Figure 5:
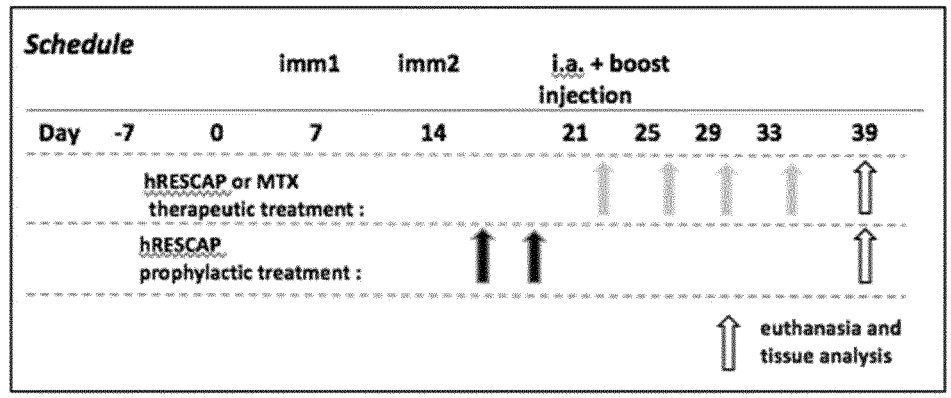
Figure 5:
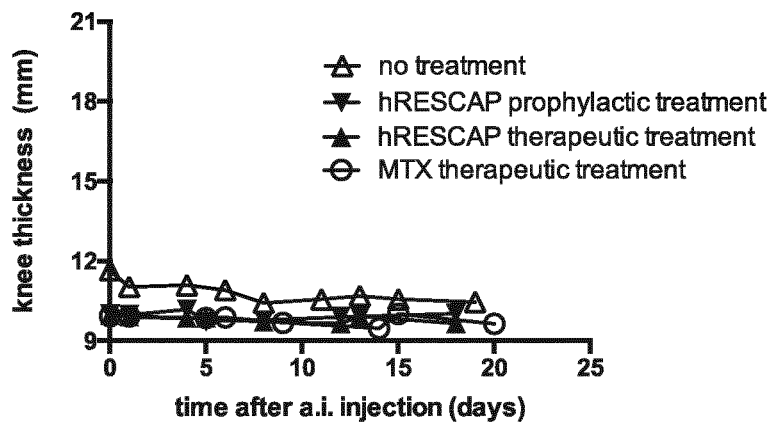
Figure 5:
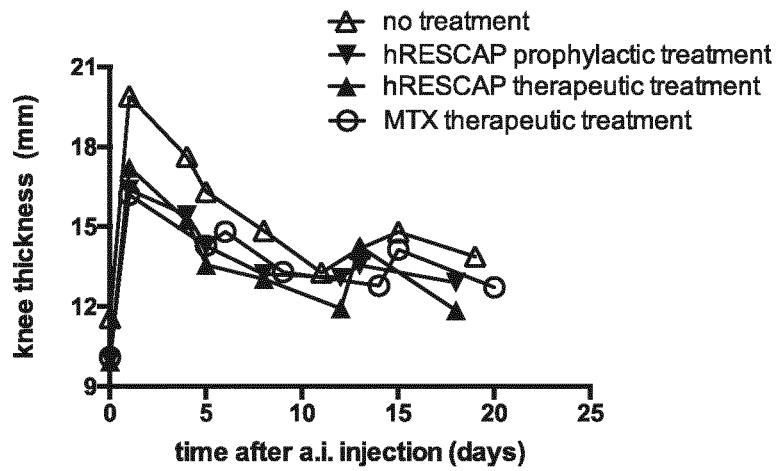

FIG. 5: shows the swelling of the knee (in millimeters (mm)) of the rats: study in group of rats that were therapeutically treated 4 times with intra articular injections. The black line through the open triangles refers to the positive control. The swelling in the left untreated knee in these rats is mild (FIG. 5A). Swelling of treated right knee is obvious (FIG. 5B). Reduced swelling is observed both after prophylactic and therapeutic AP treatment or MTX treatment upon intra articular mBSA injection into the right knee. Note that the beneficial effect of both AP and MTX on the non-treated left knee is also evident as swelling is reduced when compared to positive control treatment.

Figure 6:
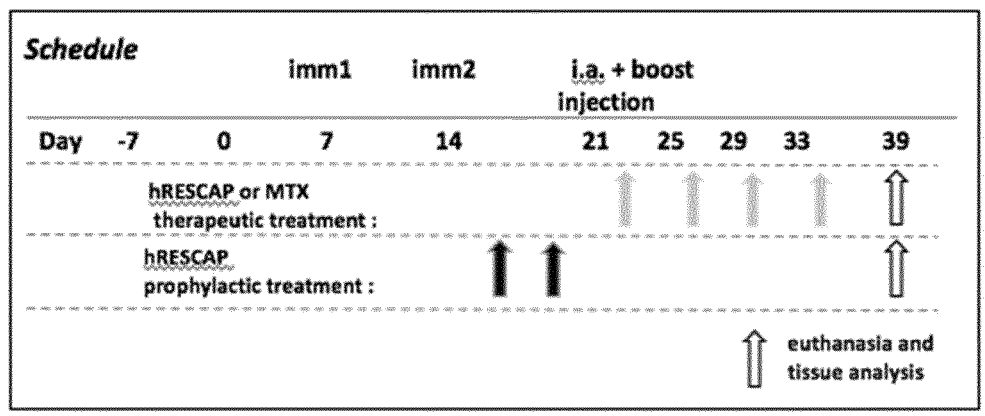
Figure 6:
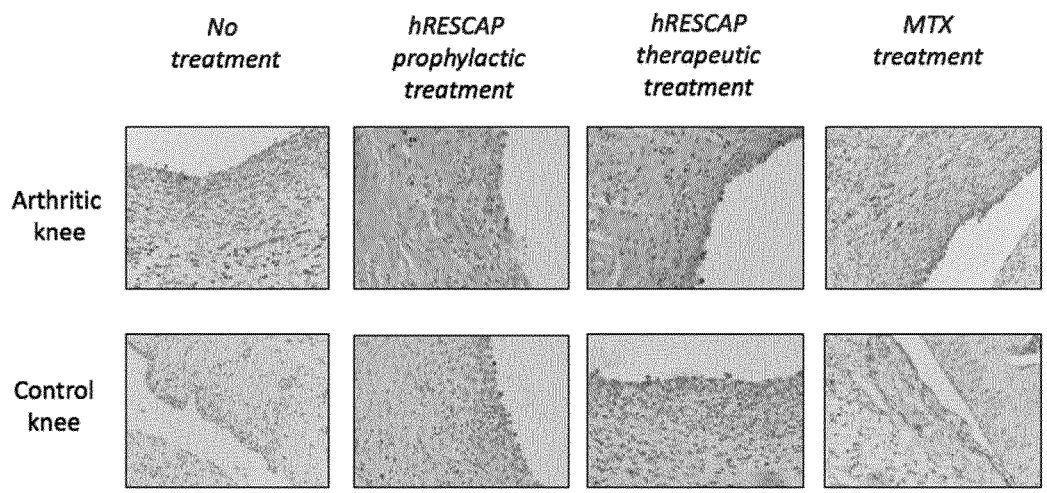

FIG. 6: shows the immunohistochemical localization and quantification of ED1+ macrophages in the synovial tissue of the rheumatoid arthritic knee of groups of rats that were either untreated, prophylactically treated or therapeutically treated with AP (i.e. hRESCAP) or therapeutically treated with MTX. The untreated rheumatoid arthritic knee contains a large number of ED1+-positive macrophages, which are largely absent in the control knee. The amount of ED1+ macrophages in the arthritic knee is very much reduced both after prophylactic and therapeutic AP treatment or MTX treatment.

Figure 7:
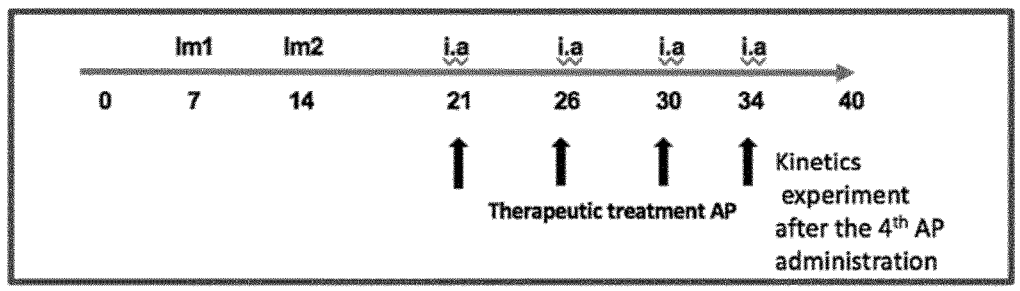
Figure 7:
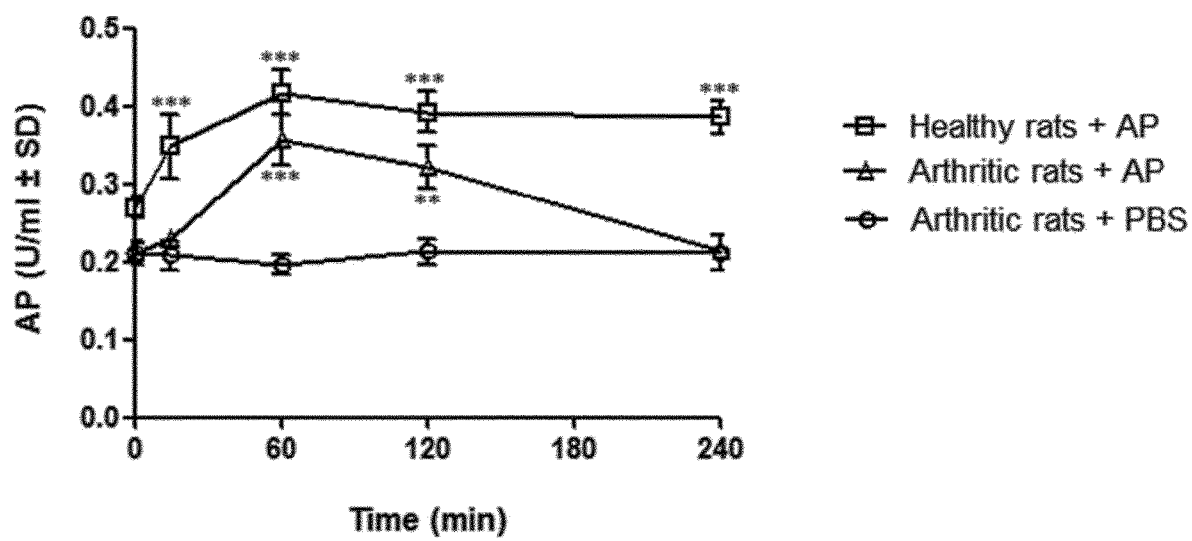

FIG. 7: Shows the AP plasma pharmacokinetics in healthy and arthritic rats. (A) shows the treatment schedule and time of pharmacokinetic measurements. Healthy and arthritic rats were administered 700 U/kg human recombinant AP, and (as control) arthritic rats received an injection with PBS. (B) Blood samples were drawn at baseline and 15, 60, 120 and 240 min after an AP injection, after which plasma samples were processed for AP enzymatic activity assays. Results are presented as mean ±SD for 2 rats per group and assays performed in duplicate.

Figure 8:
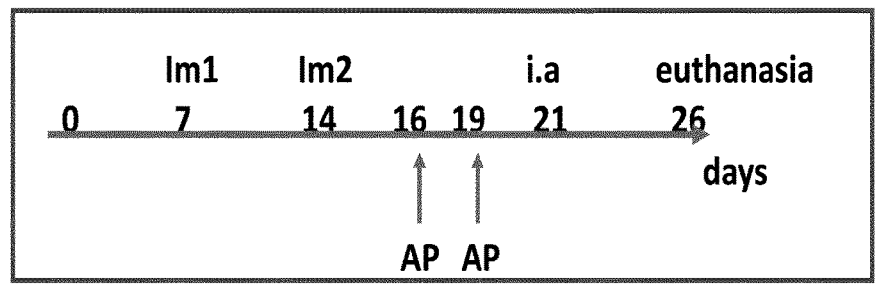
Figure 8:
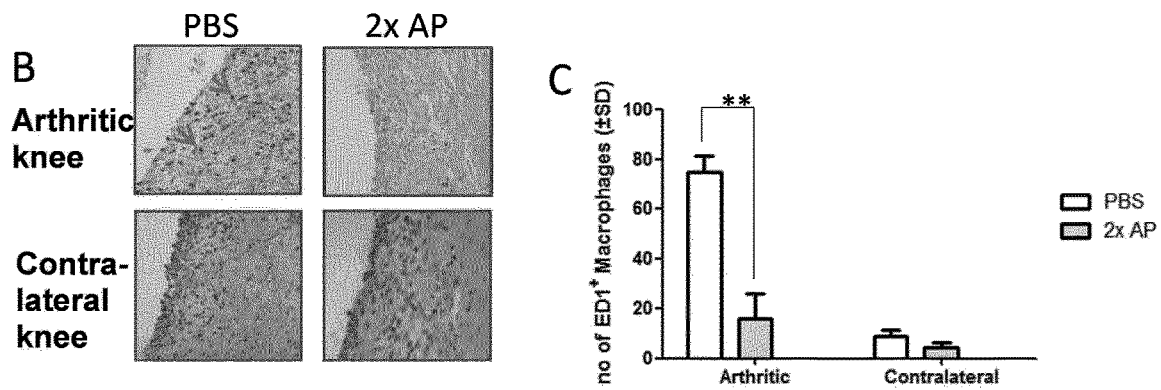
Figure 8:
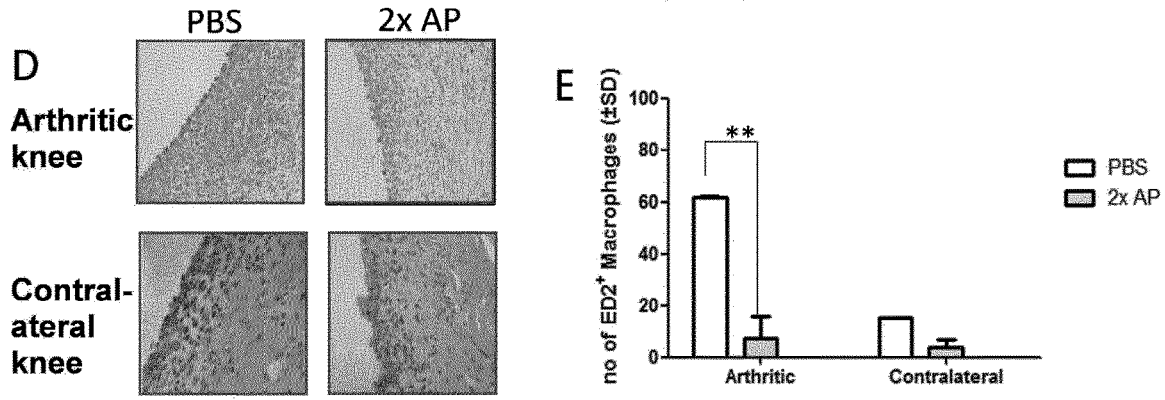

FIG. 8: Shows representative images and quantification of ED1- and ED2-positive macrophages in knee sections of rats receiving AP (2×) as prophylactic treatment. (A) shows a timeline of arthritis induction in rats and prophylactic intervention with alkaline phosphatase. On d7 and d14, the 1st and 2nd immunization (Im1 and Im2) with mBSA was performed; on d21 an intra-articular (i.a) injection was given. Prophylactic treatment with AP or PBS was given at day 16 and day 19. (B) shows ED1 images of arthritic and contralateral knees of untreated and 2× AP treated rats. (C) Quantification of ED1+ macrophages of untreated and 2× AP treated rats. (D) ED2 images of arthritic and contralateral knees of untreated and 2× AP treated rats. (E) Quantification of ED2+ macrophages of arthritic and contralateral knees of arthritic and contralateral knees of untreated and 2×AP treated rats. Error bars indicate SD.

Figure 9:
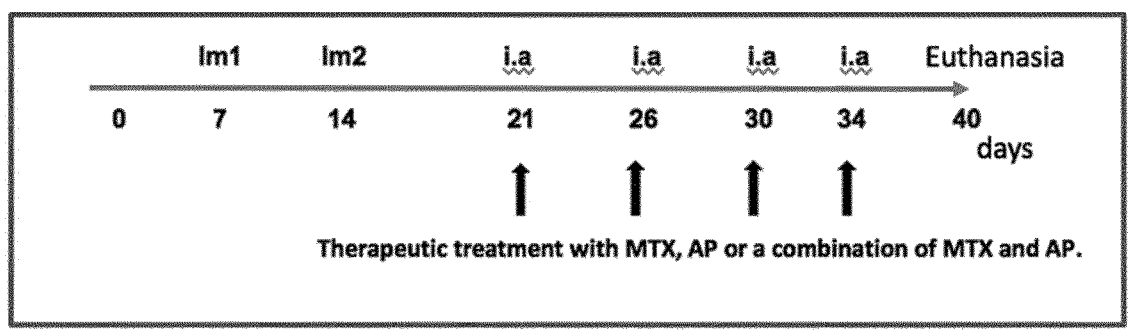
Figure 9:
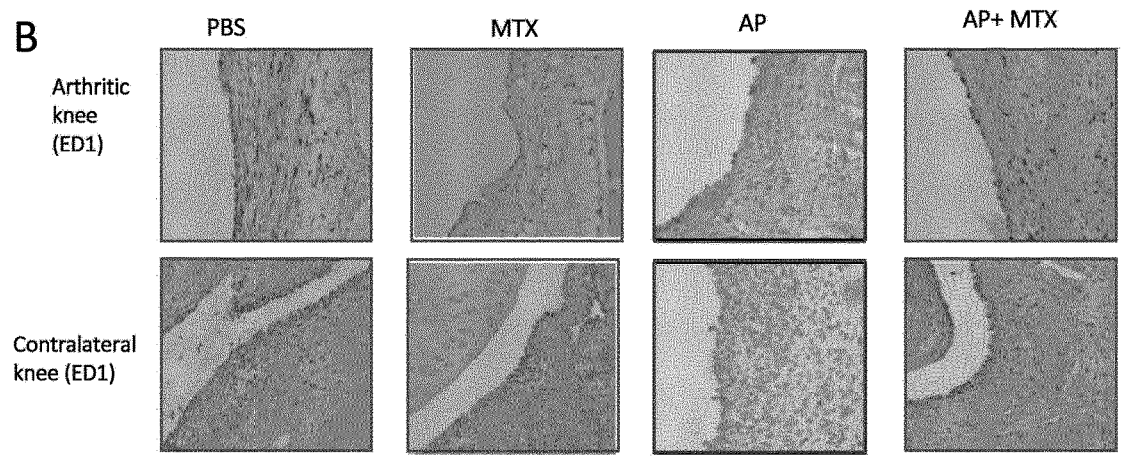
Figure 9:
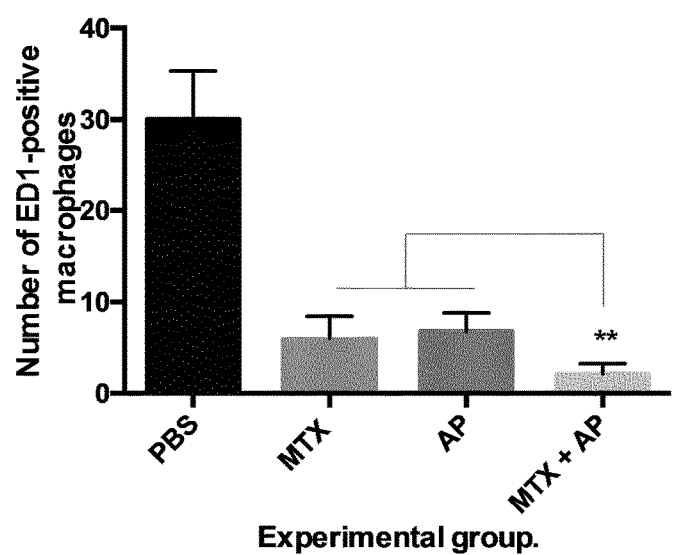

FIG. 9: Shows representative images and quantification of ED1-positive macrophages in knee sections of arthritic rats receiving AP, MTX, and AP/MTX combination therapy. (A) Treatment schedule. On d7 and d14, the 1st and 2nd immunization (Im1 and Im2) with mBSA was performed; on day 21, 26, 30 and 34 intra-articular (i.a) injections with mBSA were given. Interventions were made with AP (700 U/kg), MTX (0.3 mg/kg or 1.0 mg/kg), or AP/MTX combinations. As a control, untreated arthritic rats received injections with PBS. (B) ED1 images of healthy, arthritic and contralateral knees of PBS, MTX (1.0 mg/kg), AP (700 U/kg) and AP+MTX (1) treated rats. (C) Quantification of ED1+ macrophages of healthy, arthritic and contralateral knees of PBS, MTX, AP and AP +MTX treated rats. MTX was tested in two doses, namely 0.3 mg/kg and 1.0 mg/kg. Both doses had identical effect on the number of ED1 macrophages in the arthritic knee and therefore we grouped the results of these two experimental groups. Group sizes: PBS: n=4; MTX: n=8, AP: n=4 and MTX+AP: n=8. The combined effect of AP and MTX differed significantly from the MTX or AP alone groups (**p<0.01).

Figure 10:
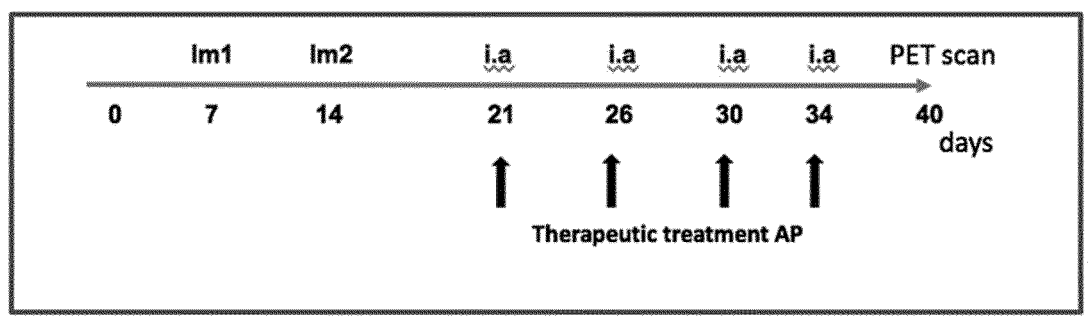
Figure 10:
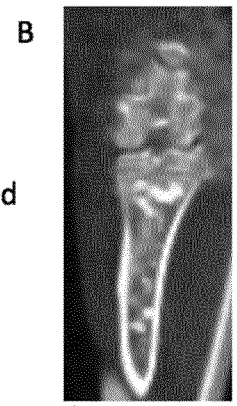
Figure 10:
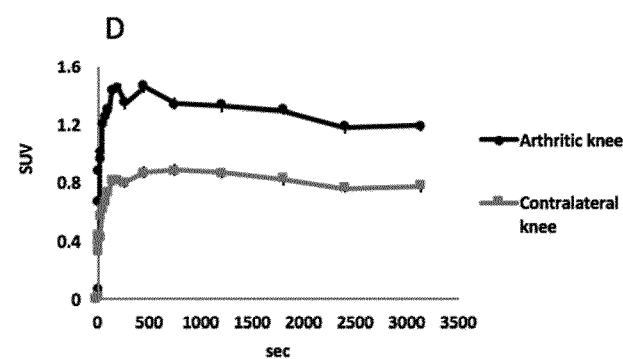
Figure 10:
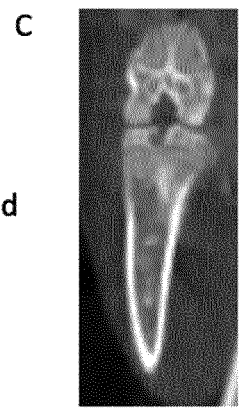
Figure 10:
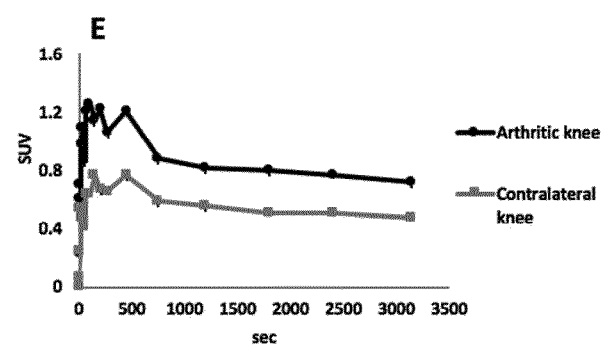

FIG. 10: Shows representative coronal PET-CT scans of [$^{18}$F]fluoro-PEG-folate in arthritic knees of (B) PBS) and (C) 4×AP treated rats. [$^{18}$F]fluoro-PEG-folate is a PET tracer that binds relatively specific to macrophages. (A) Treatment schedule. (D, E) Standardized uptake value (SUV) scale bar from min 0 to max 1, represents the uptake of the tracer. Time activity curves of [$^{18}$F]fluoro-PEG-folate uptake are expressed as SUV in arthritic and contralateral knees of the (D) untreated (only PBS) and (E) 4×AP treated arthritic rats. PET scans were made at day 40 of the experiment.

Figure 11:
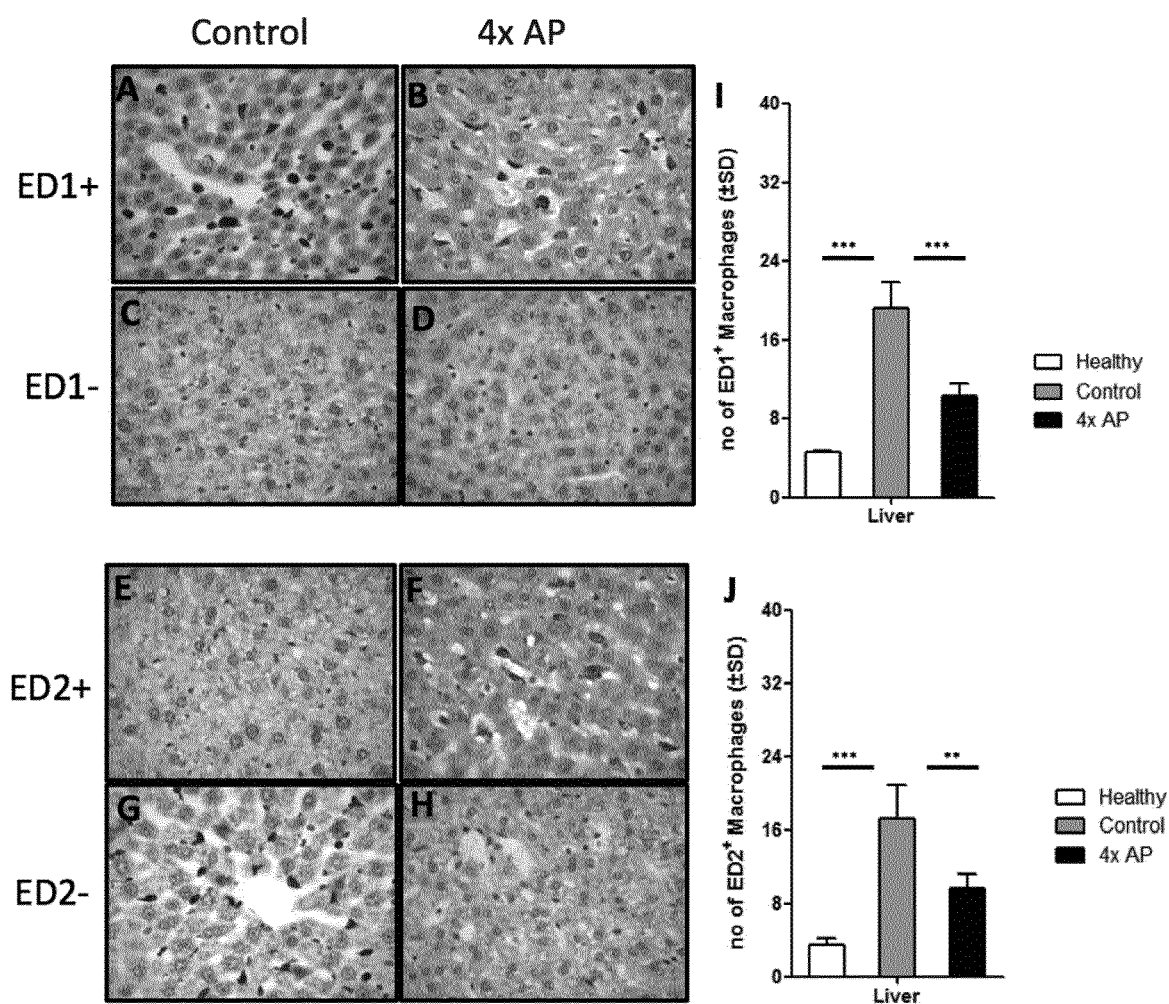

FIG. 11: Shows representative immunohistochemical (HE) images of ED1+ and ED2+ macrophages in liver sections of healthy rats, PBS-treated (control) arthritic rats and AP-treated arthritic rats. (A, B): ED1+macrophages in liver of PBS-treated and AP-treated arthritic rats, respectively. (C, D): Isotype control stained liver sections of PBS-treated and AP-treated arthritic rats, respectively. (E, F): ED2+ macrophages in liver of PBS-treated and AP-treated arthritic rats, respectively. (G, H): Isotype control stained liver sections of PBS-treated and AP-treated rats, respectively. (I, J): Quantifications of ED1+ and ED2+ macrophages in liver of healthy, PBS-treated and AP-treated arthritic rats. Values depict mean number of macrophages counted in predefined areas of the liver. Error bars indicate SD. : p<0.01, *: p<0.001.

Figure 12:
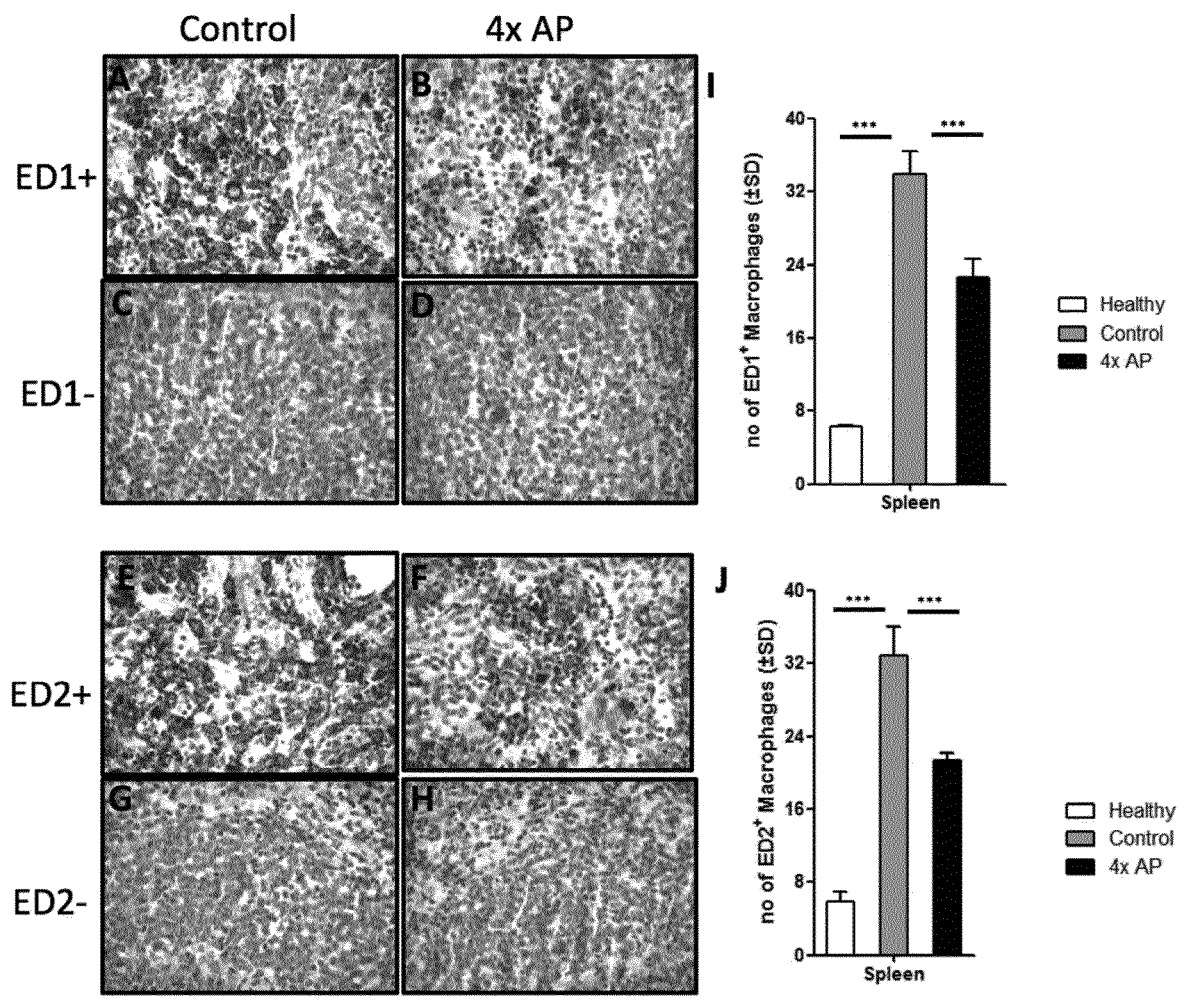

FIG. 12: Shows representative immunohistochemical (HE) images of ED1+ and ED2+ macrophages in spleen sections of healthy rats, PBS-treated (control) arthritic rats and AP-treated arthritic rats. (A, B): ED1+ macrophages in the spleen of PBS-treated and AP-treated rats, respectively. (C, D): Isotype control stained spleen sections of PBS-treated and AP-treated rats, respectively. (E, F): ED2+ macrophages in the spleen of PBS-treated and AP-treated rats, respectively. (G, H): Isotype control stained spleen sections of PBS-treated and AP-treated rats, respectively. (I, J): Quantifications of ED1+ and ED2+ macrophages in spleen of healthy, saline-treated and AP-treated rats. Values depict mean number of macrophages counted in predefined areas of the spleen. Error bars indicate SD. ***: p<0.001.

EXAMPLE 1

Rheumatoid Arthritic Knee

Impact of hRESCAP (AP Treatment) on Synovial Macrophage Infiltration in Arthritic Rats Experiments were performed using a rat model for RA as published by Chandruputla et al. (BioMed Int, 2015) to show the effects of recombinant human alkaline phosphatase (hRESCAP) on RA. hRESCAP was compared with MTX used as a positive control. The antigen-induced rat model uses two subcutaneous immunizations with a mixture of methylated bovine serum albumin (mBSA), CFA (complete Freund's adjuvant antigen) and CBP (custom Bordetella pertussis antigen) and intra-articular injections of mBSA on one side knee and saline (negative control) on the counter knee. Immunohistochemical (IHC) analysis specifically focussed on infiltration with macrophages and knee swelling is followed over time after therapeutic treatment with MTX, or hRESCAP.

In the rat model, RA is induced in the right knee (RA knee), the contralateral left knee serves as a internal control (control knee). The model allows various options for therapeutic interventions, either before intra-articular injections or during boosts injections with mBSA. Dosing of hRESCAP (700 U/kg, i.p.) was administered in different schedules as indicated in the figures. Two hours prior to AP administration, rats received a dose of levamisole (50 mg/kg, s.c.). For comparison, arthritic rats received treatment with methotrexate (1 mg/kg, i.p.).

At the end of the experiment, rats were sacrificed and knees were decalcified and processed for IHC analysis of synovial macrophage infiltration, including 2 rat macrophage antibodies; ED1 (homolog of human CD68) and ED2 (homolog of human CD163, a proposed marker for human M2 anti-inflammatory macrophages). IHC analysis of ED1 and ED2 macrophages was performed in multiple quadrants of synovial tissue, as described by Chandruputla et al (BioMed Int, 2015). Macrophage counting included synovial lining layer (SL 1-10) and synovial sublining layers (SL 1-20).

Animals

Groups of 3-6 Wistar rats (male, 150-200 grams, Charles River International Inc, Sulzfeld, Germany) were provided with standard food, water (ad libitum) and conditions. The animal experiments performed fulfilled the criteria's of European Community Council Directive 2010/63/EU for laboratory animal care and the Dutch Law on animal experimentation. The experimental protocol was validated and approved by the local committee on animal experimentation of the VU University Medical Center (DEC PET13-07).

Arthritic Induction and Therapeutic Interventions

All rats (except healthy) were immunized and arthritis was induced via 1× or 4× intra-articular (i.a) mBSA injections, 4 or 5 days apart in the arthritic (right) knee, the contralateral (left, non-arthritic) knee serving as control knee. For therapeutic interventions, AP (human recombinant placenta AP, TNO, Zeist, The Netherlands) was administered subcutaneously (s.c.) at a dose of 700 U/kg (≈200 µg), MTX (VU University Medical Centers' Pharmacy) was administered intra-peritoneal (i.p.) at two dosages: 0.3 mg/kg (low dose) and 1.0 mg/kg (high dose). The rats were divided in 8 groups, based on different treatments and treatment schedules. In a prophylactic setting, two rats received AP twice prior to intra-articular (i.a.) arthritis induction and four rats received AP twice prior to intra-articular and 4× PBS in between i.a. injections. In the treatment groups, arthritic rats were administered AP twice or 4× after arthritis induction, either as standalone therapy or in combination with low or high dose MTX. Control rats received 500 µL of PBS (i.p.). Healthy rat did not receive arthritic induction or any treatment. At the end of study, all rats were sacrificed and tissues were excised for further processing and various analyses.

Alkaline Phosphatase Activity

An enzymatic assay was used to determine plasma concentrations of alkaline phosphatase prior to and 0-4 hours after administration a dose of 700 U/kg AP to healthy rats and arthritic rats, FIG. 7. At time points 0, 15, 60, 120 and 240 min after AP administration, a blood sample was drawn from the tail vain of the rats and transferred to a 1ml Eppendorf microtube containing heparin (454081, Greiner bio-one, Charlotte, USA) as anti-coagulant. As a control, blood was drawn at the same time points from arthritic rats that were injected a t=0 with 500 µl PBS. Eppendorf tubes were centrifuged at 3,000×g for 5 min at 4° C., after which the plasma was collected and stored at −80° C. until use.

The enzymatic assay for AP is based on the conversion of the substrate paranitrophenol-phosphate (PNP; 104105, Sigma-Aldrich, Zwijdrecht, the Netherlands) to paranitrophenol which is measured spectrophotometrically at 405 nm at 25° C. To a 3 ml reaction cuvette was added 2.9 ml substrate solution (containing final concentrations of 25 mM glycine, 10 mM MgCl2, 3 mM PNP, adjusted to pH 9.6 with NaOH). The reaction was started by adding 30 μl of plasma sample, 1:1 diluted in enzyme diluent buffer (25 mM glycine, 1 mM MgCl2, 0.1 mM ZnCl2, 10% (v/v) glycerol, adjusted to pH 9.6 with NaOH). In parallel a reference cuvette was assayed without substrate. The reaction was followed on line for 5 min at 25° C. with continuous monitoring increase of absorbance at 405 nm using a (10037-434, VWR, Radnor, Pa.<USA) spectrophotometer. From the linear phase of A405 increments, AP activity in plasma samples (in U/L) was calculated from a standard curve with serial dilutions of a human recombinant placenta AP stock solution. One Unit of activity is defined as the amount of enzyme decomposing 1 μmol of PNP/min at 25° C.

Histopathology and Immunohistochemistry

The arthritic and contralateral knees from all rats were dissected in toto and fixed for 7 days at 4° C. in 10% freshly made paraformaldehyde in PBS with 2% sucrose (pH=7.3) prior to decalcification in osteosoft (101728, Merck, Germany) for ~2.5 weeks at room temperature. Thereafter, knees were embedded in paraffin. Sections of 5 μm were cut through the centre of the joint in longitudinal direction and stained with haematoxylin and eosin (HE) to assess the degree of inflammation in synovial tissue. Liver and spleen sections from all rats were dissected and fixed in 4% paraformaldehyde for 24 h before embedding in paraffin. Sections of 5 μm were cut and stained initially with HE and then for macrophages Staining for macrophages with ED1 (homologous to human CD68), and ED2 (homologous to human CD163, a marker for M2 anti-inflammatory macrophages), or isotype control antibody was performed. Images were captured using a Leica 4000B microscope and Leica digital camera DC500 (Microsystems B. V. Rijswijk, The Netherlands).

FRβ Immunofluorescence and Microscopy

Liver and spleen tissues collected at the end of the study were snap frozen in liquid nitrogen and stored at −80° C. Tissues were embedded in appropriate media (OCT; SKU4583, Tissue-Tek, Netherlands), cut using a cryotome cryostat (−20° C.) (Leica, The Netherlands) and placed on Superfrost (4951PLUS4, ThermoFisher, The Netherlands) glass slides for immunofluorescence (IF) staining Sections of 8 μm were cut and stained with haematoxylin and eosin. Immunostaining of FRβ was performed with a mouse anti-rat FRβ antibody or isotype control antibody. Specifically, liver and spleen tissue sections were first brought to room temperature (RT) for 30 min, fixed in acetone (439126, Sigma-Aldrich, Netherlands) for 10 min (−20° C.) and air dried for 10 min (RT). A DAKO pen was used to mark the sections (S2002, DAKO, Santa Carla, Calif., USA), which were subsequently washed 3× with PBS on a shaker. Hereafter, sections were incubated with 100% fetal bovine serum (FBS) for 30 min (RT) to block non-specific binding and washed again in PBS (3×5 min). Thereafter, sections were incubated with anti-rat FRβ (1:50) in 10% FBS/PBS or with 10% FBS/PBS for 24 hours at 4° C. After washing (3×5 min in PBS on a shaker), sections were incubated for 1 hour at RT with secondary antibody goat-anti-mouse Alexa 488 (1:500) (R37120) ThermoFisher Scientific, Netherlands) in 10% FBS/PBS, air dried and mounted (2 μl of MOWIOL mounting medium (81381, Merck, Zwijndrecht, The Netherlands). The 2D IF slides were imaged with a Zeiss Axiovert 200M Marianas™ inverted microscope, (40× oil-immersion lens). The microscope, camera and data processing were controlled by SlideBook™ software (SlideBook™ version 6 (Intelligent Imaging Innovations, Denver, Colo.)).

Quantification Macrophages in Knee Sections, Liver and Spleen

All stained slides were blinded and counted by two independent observers for ED1- and ED2-positive synovial macrophages. For this, the knee section was divided into four quadrants (Q1 to Q4), each representing the joint capsule with synovial tissue lining on either side of the proximal and distal side of the bone. Under the microscope (Leica) at 400× magnification, 2-3 areas in each quadrant were counted for macrophages in the lining and sub-lining (1-10 layers) of the synovium. The average number of macrophages per area from all four quadrants were combined and depicted as total number of ED1 or ED2 macrophages (±SD).

Stained slides of liver and spleen sections of arthritic rats and AP-treated arthritic rats were blinded and counted by two independent observers for FRβ, ED1- and ED2-positive synovial macrophages. For quantification, representative areas of liver and spleen sections were divided into 4 regions, each representing a central pulp and vein, respectively. The FRβ, ED1- and ED2-positive macrophages were counted at 400× magnification as described above. The average number of macrophages per area from all four regions were combined and depicted as total number of FRβ, ED1 or ED2 macrophages. As a reference liver and spleen sections of healthy rats were analyzed as control.

[$^{18}$F]fluoro-PEG-folate and PET-CT

The macrophage PET tracer [$^{18}$F]fluoro-PEG-folate was synthesized, with a radiochemical purity of >96.5% and mean specific activity of 27.6±3.5 GBq/μmol. Untreated and 4× AP-treated arthritic were anesthetized using inhalation anaesthetics (isoflurane 2-2.5% and oxygen 0.45 volume %). The tail vein was cannulated with a poly-urethane 3 French cannula (0.7 mm×19 mm, BD Angiocath, Breda, The Netherlands). During PET-CT (Mediso nanoPET-CT, Budapest, Hungary) rats were place in an integrated heating bed (~35° C.) while monitoring respiratory function. Computed tomography (CT) scan was performed for 5 min, followed by tracer administration (10.7±1.8 MBq) at the start of a dynamic PET scan of 60 min. PET data were normalized, and corrected for scatter, randoms, attenuation, decay and dead time. The list mode PET data were rebinned in 19 successive frames (4×5, 4×10, 2×30, 3×60, 2×300, 3×600 and 1×900 s), which were reconstructed using an iterative 3D Poisson ordered-subsets expectation-maximization algorithm with 4 iterations and 6 subsets. Resulting images had a matrix size of 225×225×236 voxels, each with a dimension of 0.4×0.4×0.46 mm3 Images were analysed using AMIDE software (A Medical Image Data Examiner, version 0.9.2) and were expressed as standardized uptake values (SUV). The CT and PET images were superimposed for drawing the regions of interest (ROI). Using the last frame fixed size ellipsoidal shaped ROI (dimensions: 7×4×8 mm3) were manually drawn over the area of both arthritic and contralateral knees. The time activity curve (TAC) was extracted by projecting the ROI's onto the dynamic image sequence. TACs were expressed as standardized uptake values (SUV), i.e. mean ROI radioactivity concentration normalized to injected dose and body weight.

Ex Vivo Tissue Distribution Studies

At the end of the treatment period, arthritic rats receiving 4× AP, 4× AP/low dose MTX, 4× AP/high dose MTX treatment, and untreated rats, were administered with [$^{18}$F] fluoro-PEG-folate tracer. Sixty minutes after tracer administration, rats were sacrificed. Low and high dose MTX treated arthritic rats were sacrificed without tracer administration. Upon sacrificing, all rats were excised and knees, blood and various internal organs were collected, rinsed, dipped dry, weighed and the amount of radioactivity determined using an LKB 1282 Compugamma CS gamma counter (LKB, Wallac, Turku, Finland). Results for tracer uptake in the various tissues were expressed as percentage of the injected dose per gram tissue (%ID/g).

Statistical Analysis

Statistical analysis was performed using SPSS (version 15) for Windows (SPSS INc, Chicago, Ill., USA). The Wilcoxon signed rank (exact) test was used to determine differences in paired observations, such as macrophage infiltration in arthritic versus contralateral knees. Mann-Whitney (exact) tests were performed to analyse differences in macrophage infiltration in groups; arthritic versus and PBS treated knees. A p-value<0.05 was considered as statistically significant. All results are presented as mean±standard deviation (SD).

RESULTS

Arthritis Induction and AP/MTX Therapeutic Interventions

Arthritis induction in rats was associated with macroscopic thickening of the arthritic knee compared with the contralateral control knee (data not shown). Therapeutic interventions with AP, MTX, or their combination were well tolerated and not associated with any adverse effects, nor were significant changes in the body weight observed.

Alkaline Phosphatase Pharmacokinetics Plasma AP-pharmacokinetics were assessed in healthy rats and arthritic rats following i.p. injection of 700 U/kg human recombinant placenta AP, the amount of AP used in therapeutic interventions depicted in FIG. 7 A, B. As a control plasma AP levels was determined in arthritic rats injected with PBS. Baseline plasma levels of AP were slightly higher in healthy rats (0.27±0.01 Uml) than in arthritic rats (0.21±0.02 U/ml), (FIG. 7 B). After AP administration, plasma AP levels increased over 1 hour to reach a maximum 1.5-1.7 fold increase over baseline levels in healthy and arthritic rats, respectively. Of note, increased plasma levels of AP levels in healthy rats were retained for up to 4 hours, in arthritic rats, AP plasma levels steadily returned to baseline levels. The AP levels in PBS-injected arthritic rats were unchanged over the 4 hour sampling time frame (FIG. 7B).

Effect of AP, MTX and AP/MTX Combination Therapy on Synovial Macrophage Infiltration The ability of AP, MTX and AP/MTX to suppress synovial macrophage infiltration in knee joints of arthritic rats was used as a primary endpoint for therapy efficacy assessment. To this end, macrophage numbers were quantified in arthritic knee section versus the contralateral knee section of arthritic rats by immunohistochemical assessment of the abundance of total ED1-positive macrophages and ED2-positive macrophages, the latter being representative marker for anti-inflammatory macrophages. Representative images and quantification of ED1- and ED2-positive macrophages in arthritic and contralateral knee sections, before and after therapeutic interventions, are shown in FIGS. 8 and 9. First, twice over AP administration prior to intra-articular mBSA injection elicited potential prophylactic activity by suppressing arthritis induction as indicated by a markedly reduced infiltration of both ED1+ (FIG. 8B) and ED2+ (FIG. 8D) macrophages in the arthritic knees. This was confirmed by 4-fold (p<0.01) and 8-fold (p<0.01) lower quantifications of ED1+ macrophages (FIG. 8C) and ED2+ macrophages (FIG. 8E) in arthritic knees of AP-pre-treated arthritic rats as compared to untreated rats (1× i.a.). These reduced levels were comparable to macrophage counts in contralateral knees. 2× AP administration (followed by 4× PBS) resulted in a 2-fold (p<0.01) and 3-fold (p<0.01) reduction of synovial ED1+ and ED2+ macrophage infiltration in arthritic knees of the rats. In a therapeutic setting, 4× AP administration further reduced these macrophage counts in arthritic knees by another ~8-fold (<0.001). Next, we examined the effect on synovial macrophage infiltration of AP treatment in combination with MTX. For this either an effective dose of 1 mg/kg MTX and a lower dose of 0.3 mg/kg MTX was tested. AP/MTX combinations were well tolerated and slightly increased further reductions in synovial macrophage counts were observed for AP/MTX combinations when compared to standalone MTX or AP treatment (FIG. 9).

[$^{18}$F]fluoro-PEG-Folate Macrophage PET Imaging

To examine whether the AP-treatment induced reduction of synovial macrophage infiltration in arthritic rats could also be monitored by PET imaging, a PET scan was made with macrophage tracer [$^{18}$F]fluoro-PEG-folate for one of the 4× AP-treated rats and compared with an untreated (only PBS) arthritic rat (FIG. 10). The coronal PET-CT image visualizes higher tracer uptake in the untreated arthritic rats (FIG. 10A) compared to the 4× AP-treated rats (FIG. 10B). Standard uptake values (SUV) of [$^{18}$F]fluoro-PEG-folate were quantified in the synovial region of interest (coloured ellipsoid) demonstrating increased (1.5-fold) tracer uptake in the arthritic knee of the untreated rat (FIG. 10C) as compared to the arthritic knee of 4× AP-treated rats (FIG. 10D).

Ex Vivo Tissue Distribution Studies

The impact of standalone AP treatment or combined with MTX on [$^{18}$F]fluoro-PEG-folate tracer uptake in other tissues is depicted in Table 1. In all treatment groups, [$^{18}$F] fluoro-PEG-folate was rapidly cleared from plasma (Table 1). Notably, AP and AP/MTX treatments also showed reductions of [$^{18}$F]fluoro-PEG-folate uptake in high macrophage resident organs, i.e. lung, heart, liver and spleen (Table 1). Consistent with high expression of folate receptor α in kidney and intestine tracer uptake was high in these organs, but not impacted by AP and AP/MTX treatments.

TABLE 1

Ex vivo tissue distribution of [$^{18}$F]fluoro-PEG-folate in various tissues 4x PBS (control groups), 4x AP (4AP), 4x MTX (0.3) + 4x AP (4AP + 0.3MTX) and 4x MTX + 4x AP (4AP + 1MTX) treated rats at 60 min post tracer injection. Results are expressed as mean percentage injected dose per gram (% ID/g) ± SD (n = 4 per group).

| Tissue | PBS | | 4AP | | 4AP + 0.3 MTX | | 4AP + 1MTX | |
| --- | --- | --- | --- | --- | --- | --- | --- | --- |
|  | Avg | SD | Avg | SD | Avg | SD | Avg | SD |
| Plasma | 0.010 | 0.001 | 0.010 | 0.001 | 0.032 | 0.015 | 0.011 | 0.003 |
| Blood | 0.007 | 0.001 | 0.007 | 0.001 | 0.019 | 0.013 | 0.012 | 0.004 |
| Lung | 0.184 | 0.017 | 0.111 | 0.022 | 0.096 | 0.031 | 0.094 | 0.023 |
| Heart | 0.157 | 0.008 | 0.117 | 0.024 | 0.117 | 0.030 | 0.067 | 0.046 |
| Liver | 0.235 | 0.038 | 0.151 | 0.048 | 0.162 | 0.064 | 0.149 | 0.063 |
| Spleen | 1.028 | 0.094 | 0.779 | 0.105 | 0.696 | 0.359 | 0.487 | 0.153 |

Impact of AP on Systemic Inflammation in Arthritic Rats

To examine whether the reduced tracer uptake in liver and spleen of AP-treated arthritic rats is associated with reduced macrophage infiltration in these organs, ED1 and ED2 immunohistochemistry was performed on liver (FIG. 11) and spleen (FIG. 12) section of saline-treated vs AP-treated arthritic rats with liver and spleen tissue of healthy rats as a reference. Representative images of ED1- and ED2-positive macrophages in liver and spleen sections are shown in (FIG. 11A-H) and (FIG. 12A-H), respectively. Quantifications of ED1- and ED2-postive macrophages in liver (FIG. 11 I/J) and spleen (FIG. 12 I/J) showed significantly higher (~4-5 fold, p<0.01) level in the organs of arthritic rats compared with to those of healthy rats, pointing to a systemic inflammatory component. Following AP treatment a marked and significant decrease (~50%, p<0.001) of both ED1- and ED2-positive infiltrating macrophages was observed in liver of arthritic rats (FIG. 11 I/J). Similarly, in spleen of arthritic rats, AP treated also resulted in a significant reduction (~30%, 0.001) of both ED1- and ED2-positive infiltrating macrophages was observed in liver of arthritic rats (FIG. 11 I/J. Antibody control stained liver and spleen sections were clearly negative for both ED1- and ED2-positive macrophages (FIGS. 11 & 12 C,D,G,H). These results underscore that AP establishes systemic anti-inflammatory effects by reducing macrophage infiltration in liver and spleen of arthritic rats.

CONCLUSION

Here we have shown that interventions with alkaline phosphatase (AP) elicited prophylactic anti-arthritic activity in rats by suppressing arthritis induction after intra-articular antigen injection. Moreover, in a therapeutic setting, i.e. after arthritis induction, AP intervention also conveyed local anti-arthritic effects represented by a marked reduction of synovial macrophage infiltration in arthritic rats as well as systemic anti-arthritic effects as represented by lowered macrophage infiltration in liver and spleen of arthritic rats. Lastly, AP preserves activity in treatment combinations with MTX.

Multiple interventions with human recombinant placenta AP (hRESCAP) spaced for 4 days were well tolerated by arthritic rats. A once every 4 day schedule was designed taken into account the half life time of hRESCAP in rats of≈3 days. Monitoring AP plasma pharmacokinetics after a single i.p. dose of 700 U/kg AP in healthy and arthritic rats showed peak plasma levels after 1 hour of 50-70% above baseline (FIG. 7). Other than for healthy rats, the supplemented hRESCAP remained stably higher above control level in plasma over 4 hours, whereas in arthritic rats plasma levels dropped to basal levels within 4 hours. These results confirm previous data on consumption of available AP during condition of oxidative stress, like in RA, and confirming results reported in human clinical trials. During its action AP is consumed, proposedly by conjugating to its ITM substrates, and being eliminated by Kupffer cells. Consistently, this mode of action may also be involved in the prophylactic activity of AP in dampening antigen-induced arthritis induction in the rats. Acting as an anti-inflammatory protein, the net effect of AP will be to prevent pro-inflammatory cytokines like TNFα and IL6 to be produced by activated immune cells, thereby preventing downstream effects in the inflammatory cascade. The same mode of action of AP may contribute to the therapeutic activity of AP in rats with established arthritis and reflected by reduced macrophage infiltration in the synovium. Removal of ITM's will suppress production of pro-inflammatory cytokines and reduce chemotaxis to attract monocyte/macrophage cells. Additionally, systemic and local inflammation come with increased vascular permeability and leucocyte extravasation. In this regard, AP has also been implicated to improve barrier dysfunctions by restoring tight junctions between polarized cells, thereby attenuating cell migration.

Inflamed RA synovium is characterized by the presence of polarized macrophages covering a spectrum of pro-inflammatory (so-called M1-type) and anti-inflammatory macrophages (so-called M2-type). AP interventions impacted both ED1- and ED2-positive macrophage infiltration in the synovial tissue. ED2 represents the rat homologue of human CD163, which has been assigned a marker for M2-type macrophages. This classification may not be that rigid since M2-marcrophages in an arthritic synovial microenvironment with ACPA antibodies and complex IgG autoantibodies were found to produce pro-inflammatory cytokines. AP may thus impact synovial infiltration of polarized inflammatory macrophages.

Since many cDMARD and bDMARD treatments in RA are combined with MTX, we tested the efficacy of AP and MTX combinations in arthritic rats. AP/MTX combinations were well tolerated and more effective in terms of reducing synovial macrophage infiltration. This was previously demonstrated for the 1.0 mg/kg MTX dose, but also applied for a lower dose of 0.3 mg/kg MTX, indicating that MTX dosages can be further reduced to identify the schedule for optimal efficacy in combination with AP. Conceivably, AP synergizes with the mode of action of MTX by complementing the extracellular conversion of pro-inflammatory AMP, ADP, ATP into anti-inflammatory adenosine by the action of ectophosphatases CD39 and CD73 on immunecompetent cells.

Ex vivo tissue distribution studies with the macrophage PET tracer [$^{18}$F]fluoro-PEG-folate indicate that AP and AP/MTX combinations had systemic effects beyond reducing synovial macrophage infiltration. Systemic inflammation, indicated by increased macrophage infiltration in liver and spleen, has been reported in rats with adjuvant-induced arthritis. In the present study, liver and spleen of arthritic rats also featured increased infiltration of macrophages, which were markedly decreased upon AP treatment (FIGS. 11, 12). The reduction of macrophages included FRβ-positive macrophages which constitute a marker for activated macrophages. The lowered number of FRβ-positive macrophages after AP treatment may account for reduced tracer uptake in liver and spleen in the ex vivo tissue distribution studies (Table 1). These results point to systemic anti-arthritic effects elicited by AP, which underscores systemic activity of AP observed in other animal models for inflammatory diseases.

Altogether, ectophosphatase intervention by AP fulfills a novel, unique and unmet niche in RA treatment by combining different, yet synergistic mode of actions with MTX and other cDMARDs and bDMARDs. AP as anti-inflammatory protein could be positioned in 'drug-off' periods due to discontinuation of either cDMARDs (due to development of resistance or toxicity) or biologic therapies (due to tolerisation). Given its totally different mode of action, AP can be applied as stand-alone therapeutic or can be combined with other treatment modalities, thereby establishing significant leverage in the treatment windows. Being an endogenous protein, AP lacks resistance formation or tolerisation effects. Finally, AP's potential is further supported by an extreme wide "safety window of use" and proven safety of recombinant human AP in human safety studies.

AP, both as prophylactic and as therapeutic intervention, demonstrated favourable articular and systemic anti-arthritic efficacy in a rat model of arthritis. These studies warrant further preclinical and clinical evaluation as a putative novel therapeutic entity for arthritis.

The invention claimed is:

1. A method of treating a mammal suffering from arthritis, the method comprising:
   administering to the mammal an ectophosphatase in combination with a disease modifying anti-rheumatic drug (DMARD) to treat the mammal suffering from arthritis, wherein said DMARD is methotrexate (MTX), and wherein the ectophosphatase is a tissue specific ectophosphatase selected from the group consisting of intestinal alkaline phosphatase (IAP), placental alkaline phosphatase (PALP), and liver alkaline phosphatase (LAP) and said treatment is a chronic arthritis disease treatment.

2. The method according to claim 1, wherein the arthritis is rheumatoid arthritis.

3. The method according to claim 1, wherein the ectophosphatase is selected from the group consisting of CD39, and CD73.

4. The method according to claim 1, wherein the ectophosphatase is a recombinant alkaline phosphatase.

5. The method according to claim 1, wherein the ectophosphatase is a recombinant mammalian alkaline phosphatase.

6. The method according to claim 5, wherein the recombinant mammalian alkaline phosphatase is a human alkaline phosphatase.

7. The method according to claim 1, wherein the ectophosphatase is placental ALP (PLAP).

8. The method according to claim 1, wherein the ectophosphatase in combination with a disease-modifying anti-rheumatic drug (DMARD) is further combined with nanoparticles.

9. The method according to claim 8, wherein said nanoparticles are comprised of a material selected from the group consisting of fullerene, liposome, gold, poly(lactic-co-glycolic acid) (PLGA) and poly(L-lactic acid) (PLA).

10. The method according to claim 1, wherein the administering comprises parenteral or oral administration.

11. The method according to claim 1, wherein said treating comprises prophylaxis, or delay of onset, or attenuated progression of arthritis.

12. The method according to claim 1, wherein said treating comprises attenuation of the inflammatory response of a mammal suffering from arthritis.

13. The method according to claim 1, wherein the ectophosphatase is administered at least once a month.

14. The method according to claim 13, wherein the ectophosphatase is administered at least two times a month.

15. The method according to claim 13, wherein the ectophosphatase is administered at least three times a month.

16. The method according to claim 13, wherein the ectophosphatase is administered at least four times a month.

17. The method according to claim 13, wherein the ectophosphatase is administered at least five times a month.

* * * * *